United States Patent [19]

Carr et al.

[11] Patent Number: 5,073,167
[45] Date of Patent: Dec. 17, 1991

[54] IN-LINE MICROWAVE WARMING APPARATUS

[75] Inventors: Kenneth L. Carr, Harvard; Richard S. Grabowy, Concord; Steven D. Schwaitzberg, Chestnut Hill, all of Mass.

[73] Assignee: M/A-Com, Inc., Burlington, Mass.
[21] Appl. No.: 67,626
[22] Filed: Jun. 26, 1987
[51] Int. Cl.$^5$ ............................................... A61N 5/02
[52] U.S. Cl. ................................... 604/114; 604/113; 128/804; 128/399; 606/31; 606/33; 606/34; 606/42; 219/10.55 R; 219/10.55 M; 219/10.55 F
[58] Field of Search ...................... 128/303.1, 362, 345, 128/399, 804; 604/20, 28, 93, 113, 114; 219/10.55 B, 10.55 F, 10.55 R, 10.55 M, 10.55 F; 606/27, 31-34, 41, 42

[56] References Cited

U.S. PATENT DOCUMENTS

| | | | |
|---|---|---|---|
| 2,388,830 | 11/1945 | Cotton | 128/804 |
| 2,407,690 | 9/1946 | Southworth | 128/804 |
| 3,518,393 | 11/1968 | Besseling et al. | 219/10.41 |
| 3,963,892 | 6/1976 | Camph | 219/10.55 M |
| 4,321,918 | 3/1982 | Clark, II | 604/20 |
| 4,358,652 | 11/1982 | Kaarup | 219/10.55 A |
| 4,471,192 | 9/1984 | Awata et al. | 219/10.55 |
| 4,614,514 | 9/1986 | Carr et al. | 604/113 |
| 4,632,127 | 12/1986 | Sterzer | 128/804 |
| 4,642,712 | 3/1987 | Zeipel | 219/10.55 |
| 4,652,712 | 3/1987 | Zeipel | 219/10.55 F |
| 4,660,572 | 4/1987 | Maruyama | 128/804 |
| 4,715,727 | 12/1987 | Carr | 219/10.55 A |

FOREIGN PATENT DOCUMENTS

| | | |
|---|---|---|
| 0192024 | 8/1986 | European Pat. Off. |
| 2330317 | 2/1974 | Fed. Rep. of Germany |
| 3200556A1 | 1/1982 | Fed. Rep. of Germany |
| 3428514 | 3/1986 | Fed. Rep. of Germany |

OTHER PUBLICATIONS

List of Blood Warmers Compiled by Applicant.
J. Andre, R. Barthelemy, S. Lefeuvre, A. Priou, and J. P. Morucci, *Heating Blood in Extracorporal Circulation with a High-Frequency Electromagnetic Field: Effect of Microwaves on Blood*, Biomedical Thermology, pp. 257-268, 1982.
J. S. Anshus, G. L. Endal and J. L. Mottley, *Microwave Heating of Itravenous Fluids*, American Journal of Emergency Medicine, vol. 3, No. 4, Jul. 1985, pp. 316-319.
J. F. Arens and G. L. Leonard, *Danger of Overwarming Blood by Microwave*, Journal of the American Medical Association, vol. 218, No. 7, Nov. 1971.
K. Linko, *In-Line Bloodwarming and Microfiltration Devices*, 23 23 Acta Anaesthesia Scandinavia 40, 1979.
M. S. Cherry, G. H. Hodgson and H. Nottebrock, *Comparison of Two In-Line Blood Warmers*, Canad. Anaesth. Soc. J., vol. 28, No. 2, Mar. 1981.
S. J. Fried, B. Satiani, and P. Zeeb, *Normothermic Rapid Volume Replacement for Hypovolemic Shock: An In Vivo and In Vito Study Utilizing a New Technique*, J. Trauma, vol. 26, No. 2, p. 183, 1986.
Problem UW-44-Microwave Blood Warmer for Extracorporeal Circulation, NASA Biomedical Application Team, University of Wisconsin, 1977.
K. Linko and K. Hynynen, Acta Anaesth. Scand. 1979, 23, p. 320, Erythrocyte Damage Caused by the Haemotherm Microwave Blood Warmer.
D. J. Peterson, L. M. Partlow and O. P. Gandhi, *An Investigation of the Thermal and Athermal Effects of Microwave Irradiation on Erythrocytes*, IEEE Transactions on Biomedical Engineering, vol. BME-26, No. 7, Jul. 1979.

Primary Examiner—David Shay
Attorney, Agent, or Firm—Wolf, Greenfield & Sacks

[57] ABSTRACT

A microwave apparatus for warming of a liquid such as blood or IV fluids in which the warming occurs in-line by means of a microwave heating cavity having a source of microwave energy coupled thereto. A support element in the form of a bobbin forms an assembly with an IV tube wound about the bobbin. This tubing-bobbin assembly is inserted into the microwave heating cavity. A non-invasive, non-perturbing microwave temperature monitor is provided coupled to the microwave heating cavity for monitoring the temperature of liquid flowing in the IV tube. Controls are provided including a desired operating temperature selector for combining signals representative of, not only cavity temperature, but also inlet and outlet temperatures to control the power level of microwave energy delivered to the heating cavity.

40 Claims, 6 Drawing Sheets

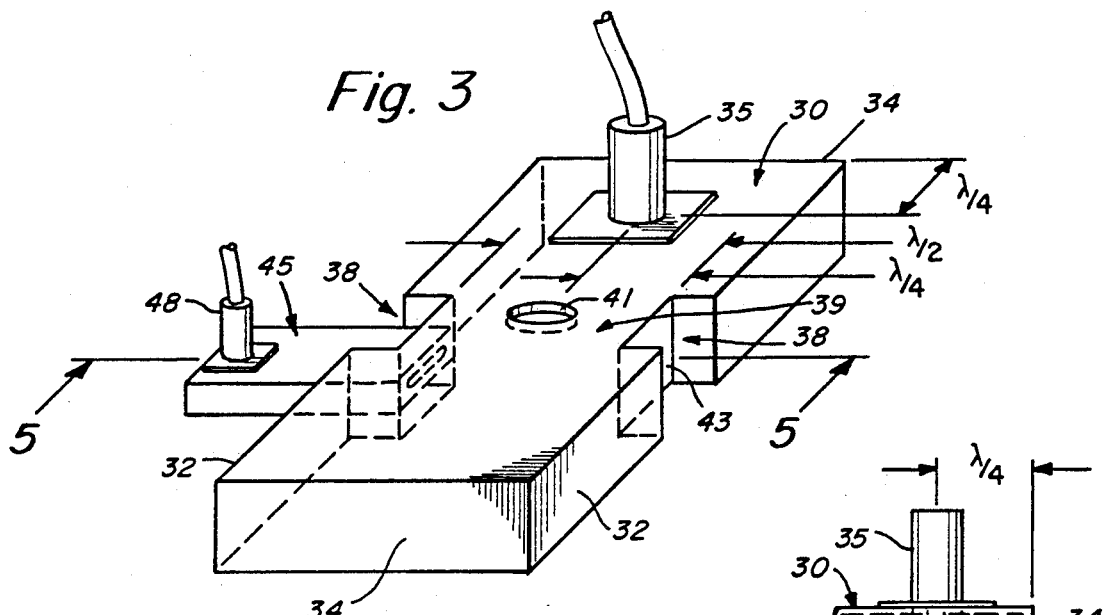
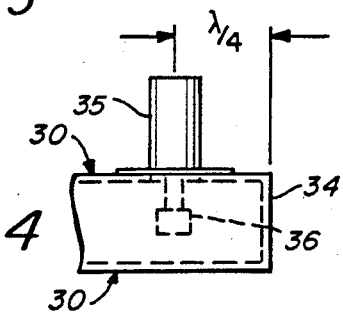
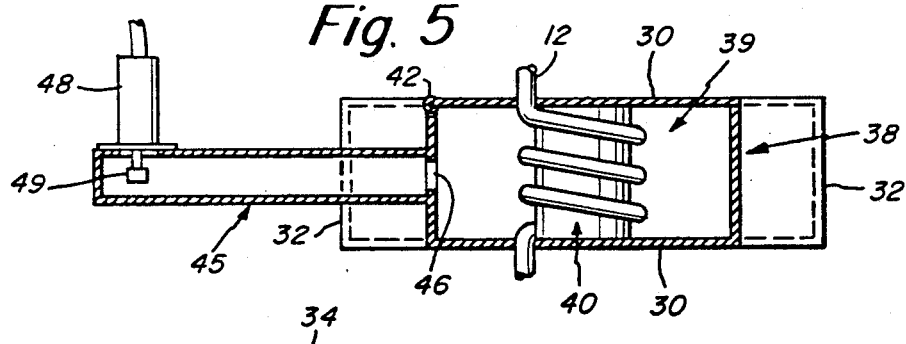
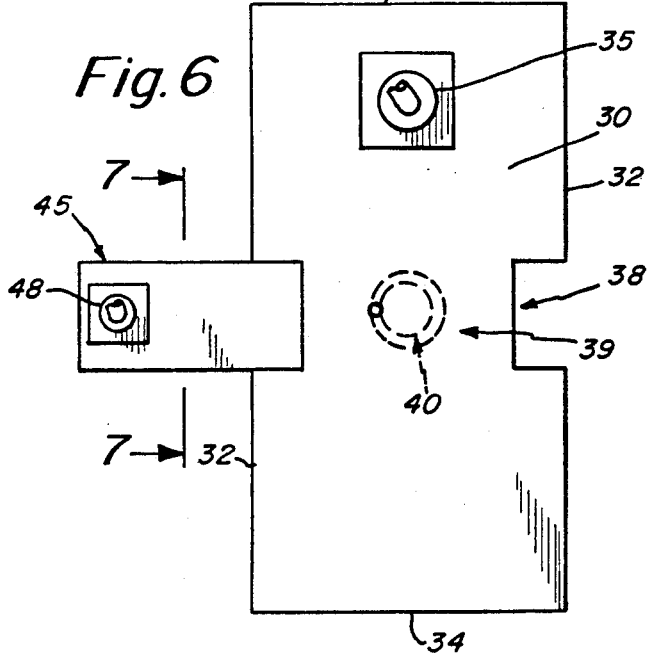
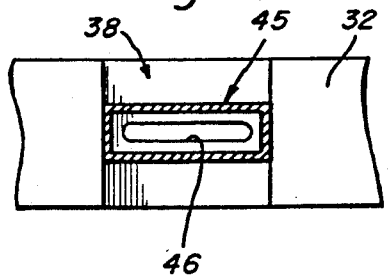

5,073,167

IN-LINE MICROWAVE WARMING APPARATUS

BACKGROUND OF THE INVENTION

1. The present invention relates in general to an in line microwave warming apparatus. More particularly, the present invention relates to a microwave warmer for blood and intravenously fed fluids. Even more particularly, the invention relates to an in line microwave warmer in combination with temperature detection apparatus preferably employing radiometric measurement of temperature.

2. Background Discussion

In the medical field there presently exists a number of applications requiring the warming of blood and in some instances, intravenously fed fluids. For example, in connection with cardiac surgery during extracorporal circulation (ECC) the patient is first cooled in order to slow metabolism and thereafter there is a requirement that the circulating blood be warmed. For a discussion of blood warming in association with cardiac surgery refer to the article "Heating Blood and Extracorporal Circulation with a High Frequency Electromagnetic Field: Effect of Microwaves on Blood" by J. Andre, R. Barthelemy, S. Lefeuvre, A. Priou and J. P. Morucci, appearing in "Biomedical Thermology", pages 257–268, Copyright 1982, Alan R. Liss, Inc., 150 5th Avenue, New York, N.Y., 10011.

The Biomedical Thermology article just referenced, employs a microwave heating unit but as indicated in the article, the electric field that is established is non uniform and thus the blood or other liquid is heated in an inhomogeneous manner.

Another medical application for the warming of blood or intravenous fluids is in a trauma situation. For example, heated intravenous fluids are useful in hyperthermic patients and in trauma patients requiring massive IV resuscitation. Clasically, hyperthermic patients are warmed either passively, if the hyperthermia is mild, or actively, if severe. In this connection the microwave heating of intravenous fluids is addressed in the article "Microwave Heating of Intraveneous Fluids" by John S. Anshus, Gerald L. Endahl and J. Lawrence Mottley.

It has furthermore been found that cardiac arrest may occur due to hyperthermia resulting from the rapid, massive transfusion of refrigerated blood. In this connection reference is made to an article relating to associated dangers of overwarming blood. This is the article "Danger of Overwarming Blood by Microwave" by James F. Arens and George L. Leonard, "Journal American Medical Association", November 15, 1971, volume 218, No. 7.

One common technique for warming blood is to pass the blood through plastic coils immersed in a warm water bath. Of course, this method has numerous drawbacks, one in particular being the slowness of operation.

Microwave heating has been employed in connection with the heating of blood and intravenous fluids. Typically, a standard microwave oven is used to warm the entire blood bag. This has not been proven successful basically because it is virtually impossible to achieve uniform heating of the blood or other liquid due to both the non uniform distribution of microwave energy within the oven and the inability, using microwaves, to heat at sufficient depths in a lossy material such as blood which has a high dielectric constant. Basically, hot spots develop causing significant blood damage. Again, in this regard refer to the previously mentioned Arens, et al article.

A further problem associated with heating the entire blood bag in a microwave oven, is the inability to monitor the temperature of the liquid particularly at depths.

OBJECTS OF THE INVENTION

Accordingly, it is an object of the present invention to provide a microwave warming apparatus that provides for the uniform heating of liquids, and in particular blood or intravenous liquids.

Another object of the present invention is to provide an improved warming apparatus that provides for the rapid heating of a liquid such as blood while flowing through an IV tube or the like.

A further object of the present invention is to provide a dynamic in-line microwave warming apparatus in which liquid temperature is monitored preferably employing a radiometer.

Still another object of the present invention is to provide an improved control system for an in line microwave warming apparatus to accurately control the heating power level based upon temperature measurements taken.

Still a further object of the present invention is to provide a control system as in accordance with the preceding object and in which multiple temperature measurements are taken preferably including inlet and outlet temperatures as well as the temperature at the heating area.

Another object of the present invention is to provide an improved control system as in accordance with the preceding objects in which all temperature measurements made may be through the use of a common radiometer.

A further object of the present invention is to provide an in-line microwave warming apparatus that incorporates a non-invasive, non-perturbing temperature monitoring technique particularly at the point or area of heating so as to prevent hot spots.

Still another object of the present invention is to provide, in a microwave warming apparatus employing a microwave heating cavity, an improved support means for the conduit carrying fluid that is to be heated.

SUMMARY OF THE INVENTION

To accomplish the foregoing and other objects, features and advantages of the invention there is provided microwave a apparatus for the warming of a liquid flowing in a liquid conduit. The microwave apparatus of the present invention is in particular used for the warming of blood or intravenous fluids typically flowing in an IV tube. The microwave apparatus of the present invention operates on a dynamic concept providing for in line warming of the liquid. In accordance with the present invention the microwave apparatus is comprised of a microwave heating cavity having coupled thereto a source of microwave energy. Means ar provided for supporting a length of the liquid conduit disposed in the microwave heating cavity. In the preferred embodiment of the invention, the means for supporting the conduit comprises a bobbin means adapted to receive the liquid conduit wound about the bobbin means. The bobbin means is preferably a discardable item. The microwave apparatus of the present invention also includes non-invasive, non perturbing microwave temperature monitoring means coupled to the microwave heating cavity for monitoring the temperature of liquid flowing in the liquid conduit at the heating cavity. In more particular, regarding the present invention, the microwave heating cavity comprises a first waveguide member and a preferred coax-to-waveguide transition for coupling the microwave energy to the microwave heating cavity including a probe disposed at one end of the first waveguide member. The first waveguide member preferably has a restricted portion disposed along its length defining a concentrated and uniform heating area at which is disposed the bobbin means. The temperature monitoring means, preferably comprises a second wave guide member coupled into the heating area of the microwave heating cavity. The first waveguide member has at least one wall thereof that may be opened and closed so as to receive the bobbin means and so as to enable removal thereof. As far as the restricted portion of the first waveguide member is concerned, this is preferably disposed midway therealong.

For the sensing of temperature that is to be monitored, a radiometer circuit is employed coupled from the second waveguide member for sensing temperature at the heating area. The radiometer circuit connects also to the microwave source to control the output signal thereof as a function of at the least the temperature sensed at the heating area of the microwave heating cavity. The microwave source operates at a predetermined heating frequency and the sensed temperature is sensed at a different radiometer detection frequency. The detection frequency is preferably greater than the heating frequency. For example, the detection waveguide may operate at 4.7 GHz while the transmitter frequency may be 2.45 GHz.

Moreover, in accordance with the invention there is provided a third waveguide member at the inlet side of the cavity for detecting liquid inlet temperature. Also employed is a fourth waveguide member at the outlet side of the heating cavity for detecting liquid outlet temperature. Both the third and fourth waveguide members also couple to the radiometer circuit. In the preferred embodiment of the system described herein, a multiplexing or switching arrangement is employed for using the same radiometer for sensing cavity, inlet and outlet temperatures. Separate storage means is also provided for storing signals on a continuously updated basis corresponding to the temperatures at the cavity inlet and outlet. Control means are provided responsive to these temperatures that are being monitored for controlling the power level of microwave energy delivered from the microwave energy source so as to maintain the desired temperature of the liquid. In this regard the control means includes manually settable means for setting a signal indicative of the desired temperature of liquid warming.

With further particularity regarding the control means, this includes a first comparator means responsive to inlet temperature and the desired temperature for providing an intermediate power level signal. There is a second comparator means responsive to the outlet temperature and desired temperature for providing a scaling factor signal. There is also a multiplier means for receiving both the intermediate signal and the scaling signal. There is a third comparator means responsive to cavity temperature and maximum temperature for providing an inhibit signal in the event that there is a detection of cavity temperature over some predetermined maximum that is not to be exceeded. Switch means are provided controlled by this inhibit signal. The switch means is disposed at the output of the aforementioned multiplier means.

In accordance with a further aspect of the present invention there is provided a system for controlling the warming of a liquid flowing in a liquid conduit such as an intravenous tube by means of a microwave heating cavity that receives the liquid conduit and that has means for providing microwave energy thereto along with inlet and outlet sides thereof. The control system in accordance with the present invention includes means for monitoring heating cavity temperature, means for monitoring liquid temperature at the inlet and means for monitoring liquid temperature at the outlet. Means are provided for preferably manually selecting a desired operating temperature for the liquid. Control means are provided responsive to the means for selecting to combine signals representative of cavity, inlet and outlet temperatures to control the power level of microwave energy delivered to the heating cavity. The means for monitoring cavity, inlet and outlet temperatures each comprises separate waveguide means and each of these waveguide means preferably includes a waveguide-to-coax transition.

In accordance with the present invention there is also provided a method for warming a liquid flowing in a liquid conduit such as an intravenous tube by means of a microwave heating cavity having microwave energy coupled thereto from a microwave transmitter. This method comprises the steps of, providing at least a part of the heating cavity that can be opened and closed, providing a support means for a length of a liquid cavity, preferably wound about the support means and disposing this support means and wound conduit or tube in the cavity. The next step is closing the cavity and applying controlled energy to the cavity to cause liquid warming as the liquid flows through the cavity. Next is the monitoring of temperature at the cavity to control energy coupled thereto. Preferably monitoring of temperature occurs at the cavity as well as at the inlet and outlet thereto to control energy coupled to the cavity from the microwave transmitter.

Finally, in accordance with a further feature of the present invention there is provided a method of controlling the warming of a liquid flowing in a liquid conduit such as an intravenous tube by means of a microwave heating cavity that receives the liquid conduit and that has means for providing microwave energy thereto along with inlet and outlet sides thereof. This method includes the steps of monitoring heating cavity temperature, monitoring liquid temperature at the inlet and monitoring liquid temperature at the outlet. A desired operating temperature for the liquid is selected preferably manually and in response to this selection signal the temperature signals that are monitored are combined to control the power level of microwave energy delivered to the heating cavity.

BRIEF DESCRIPTION OF THE DRAWINGS

Numerous other objects, features and advantages of the invention should now become apparent upon a reading of the following detailed description taken in conjunction with the accompanying drawings, in which:

FIG. 3 is a perspective view of the heating cavity in accordance with the present invention;

FIG. 4 is a fragmentary view of the heating cavity at the power input and thereof;

FIG. 5 is a cross sectional view taken along line 5—5 of FIG. 3 illustrating the main waveguide along with the cavity temperature monitoring waveguide segment and furthermore illustrating the intravenous tube on its bobbin support means disposed in the waveguide cavity;

FIG. 6 is a plan view of the microwave heating cavity of this invention;

FIG. 7 is a cross sectional view taken along line 7—7 of FIG. 6 showing the coupling aperture from the detection waveguide into the heating waveguide member;

DETAILED DESCRIPTION

In accordance with the present invention there is provided an in-line microwave warming apparatus that can be used for the warming of blood and IV fluids. The apparatus of the present invention operates so as to eliminate hot spots in providing the warming so as not to cause any damage to the blood or IV fluids. The warming of the blood preferably occurs in an IV tubing that may typically lead from a blood storage bag to the patient. The tubing diameter is preferably small with respect to the wavelength of the heating frequency, thereby insuring uniform heating of the liquid contained within the tubing. The liquid such as blood is in constant motion through the tubing and is therefore not stationary, further minimizing the possibility of hot spots.

As indicated previously, one problem with the use of heating in a microwave oven is the inability to monitor the temperature of the liquid, particularly at depths in the liquid. However, with the technique of the present invention there is provided for the monitoring of the temperature utilizing a radiometer circuit with detection occuring at microwave frequencies. This enables the measurement at depth to occur while the liquid is in motion. Furthermore, in accordance with the present invention there is measured, in addition to the temperature at the heating cavity, also inlet and outlet temperature. Measured differential temperatures are used to determined the power level required for heating. The temperature measurement within the microwave cavity itself is preferably compared against a maximum desired temperature so that the liquid temperature within the cavity does not exceed this temperature. All three temperatures monitored are measured preferably by means of a common radiometer.

In accordance with the invention, the radiometer frequency is different from that of the heating frequency. In one example, a radiometer frequency of 4.7 GHz is used while the heating frequency is 2.45 GHz.

Figure 1:
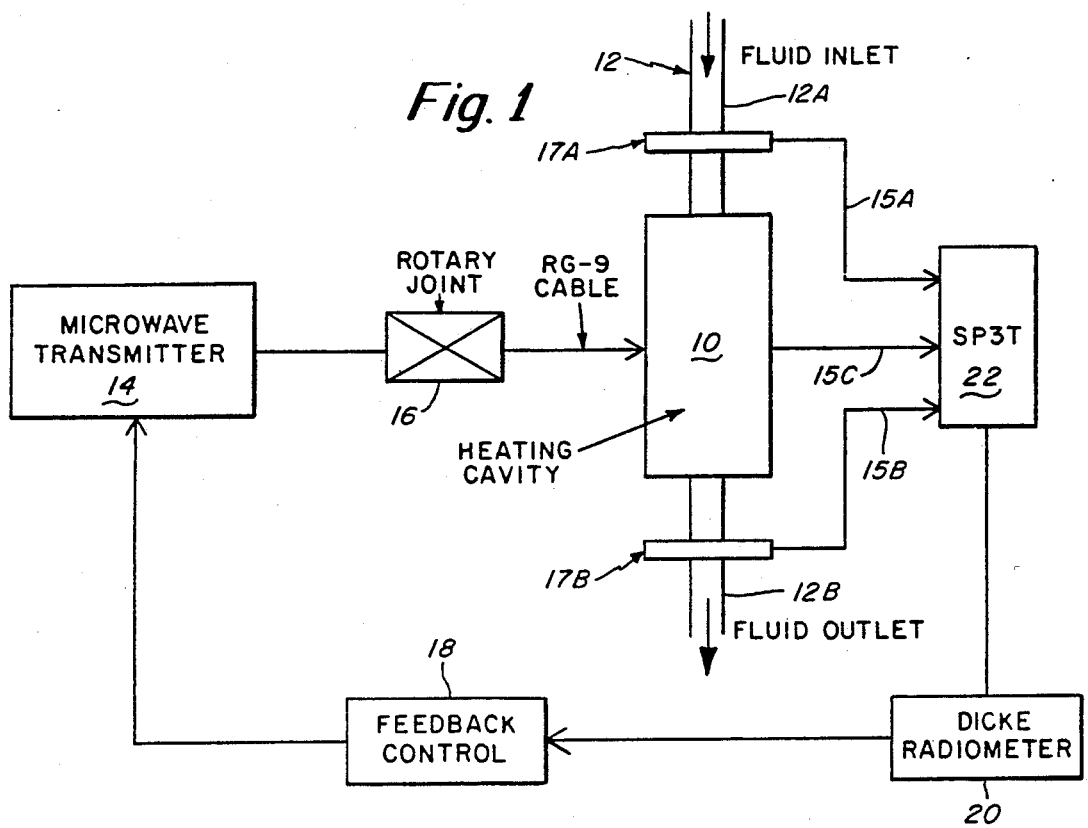
FIG. 1 is a block diagram illustrating the overall system of the present invention including the temperature monitoring along with the heating aspects thereof including furthermore the feedback control for controlling the output of the microwave transmitter.

Reference is now made to the block diagram of FIG. 1 illustrating the overall system of the present invention. At the heart of the system is the microwave heating cavity 10 through which the IV tube 12 extends. FIG. 1 shows the fluid inlet at 12A and the fluid outlet at 12B. The power that is coupled to the heating cavity 10 is from a microwave transmitter 14 that may connect by way of a rotary joint 16 employing, for example, an RG-9 cable. The microwave transmitter 14 may be of conventional design and is controlled by the feedback control 18 which in turn is controlled from temperatures being monitored from the radiometer circuit 20.

With respect to the temperature monitoring aspects of the present invention, the block diagram of FIG. 1 illustrates three lines 15A, 15 and 15C that couple waveguide generated signals by way of the switch of multiplexer 22 to the radiometer circuit 20. In FIG. 1 further details are described hereinafter in connection with FIGS. 13 15 regarding further details of the control aspects of the invention.

In FIG. 1 it is noted that the line 15C couples directly from the heating cavity 10 and thus provides a temperature to switch 22 that is representative of the temperature directly in the heating area of the microwave heating cavity. The line 15A couples from waveguide member 17A at the IV tube inlet. Similarly, line 15B couples from waveguide member 17B at the fluid outlet. A further waveguide member, not described in the block digram of FIG. 1 is employed for monitoring temperature at the heating cavity. The switch 22 in an ordered sequence couples signals from one of the lines 15A-15C to the radiometer circuit 20. These signals are thereafter stored as to be described hereinafter in connection with FIGS. 13-15.

Figure 2:
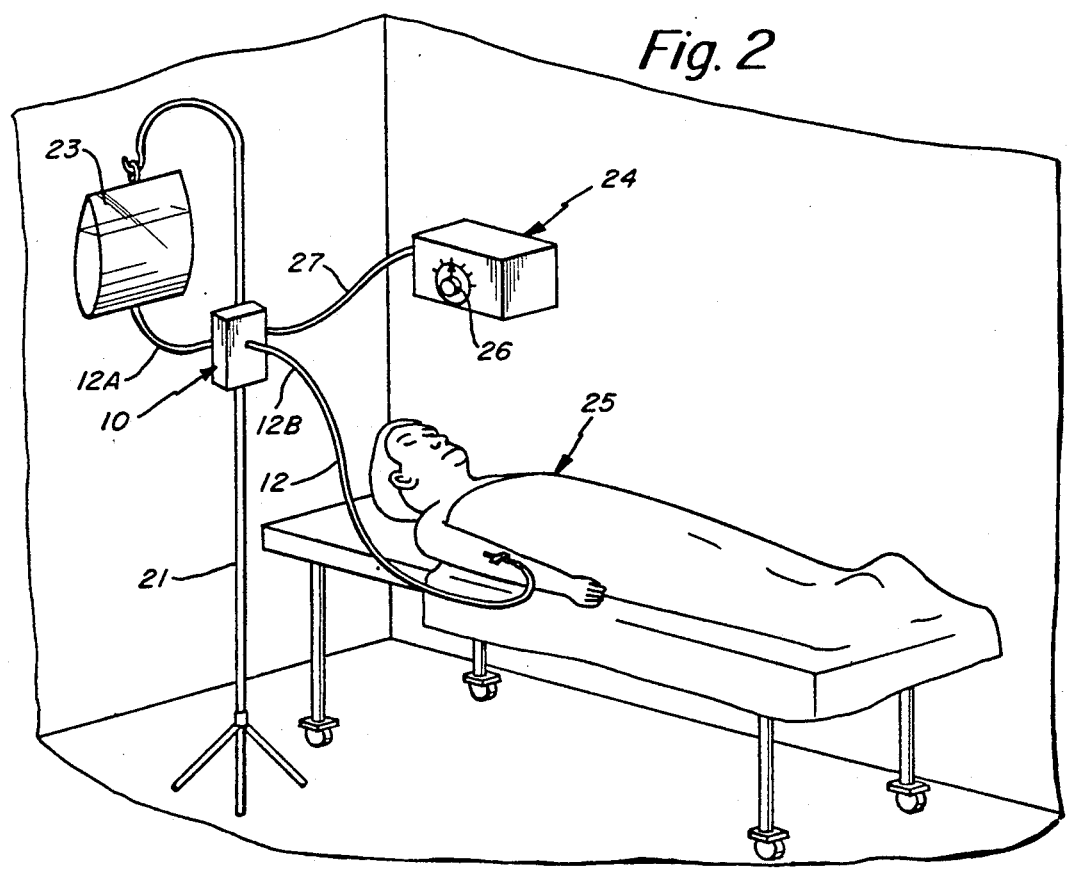
FIG. 2 is a perspective view illustrating the transfusion of blood to a patient such as in a trauma situation and employing the microwave warming apparatus of the present invention including the heating cavity and separate control and power unit.

Reference is no made to FIG. 2 illustrating the general environment in which the system and apparatus of the present invention may be employed. In FIG. 2 it is assumed that there is a patient indicated at 25 that is being intravenously fed with blood from an IV tube 12. A blood bag 23 is supported from a stand 21. The stand 21 may also support the basic heating cavity 10. The IV tube is shown being fed through the heating cavity 10 with the inlet being shown at 12A and the outlet at 12B.

FIG. 2 also shows the power and control unit 24 that is coupled by way of a cable 27 to the heating cavity 10. This cable 27 carries power from the unit 24 for providing heating energy at the microwave cavity. The cable 27 may also couple temperature monitoring signals to the unit 24 for the control of heating power. In FIG. 2 also note the dial 26 which may be used to select the desired temperature of the fluid in the IV tube 12. This would be the temperature desired at the cavity which should in substance be quite close to the temperature of the fluid coupled to the patient.

Reference is now made to FIGS. 3-7 for further specific details of the microwave heating cavity 10. This heating cavity is in the form of a waveguide member having broad walls 30, narrow walls 32, and end plates 34. The coupling of energy into the microwave heating cavity is by means of a standard coaxial-to-waveguide probe and connector. A type N connector may be employed. FIGS. 3, 4 and 6 show the input connector 35. FIG. 4 shows the probe or launch 36. The distance between the capacitor probe 36 and the end plate 34, as illustrated in FIG. 4, is approximately ¼ wavelength at the transmitter frequency.

As illustrated, in particular, in FIGS. 3 and 6, the waveguide member is reduced in cross section at 38. This is at a position midway along the length of the waveguide member as illustrated, for example, in FIG. 6. At this restricted portion 38 the waveguide has a narrow wall that does not change but the broad wall is smaller as illustrated. This restricted portion 38 defines a heating area at 39 which is adapted to accommodate the support means for the IV tube 12. This support means is in the form of a tubing-bobbin assembly including the IV tube 12 and the bobbin 40. To accommodate the tubing bobbin assembly, there may be an aperture 41 in the top broad wall 30 of the waveguide member. Alternatively, the entire broad wall 30 or a segment thereof may be hinged, such as at 42 in FIG. 5 so that it can be opened and closed to permit insertion and withdrawl of the tubing-bobbin assembly.

With regard to the tubing bobbin assembly, it is noted that the IV tubing is wound bout the bobbin 40 and the ends of the tubing may exit the bobbin both at the same end or at opposite ends thereof. For example, in the embodiment of FIG. 5 the tubing exits through the respective top and bottom broad walls 30. Some type of an interlocking arrangement may be provided for securing the ends of the tube at respective ends of the bobbin so that the assembly stays intact. It is furthermore noted that the bobbin 40 is preferably a discardable item with the rest of the waveguide heating cavity preferably being reusable.

As noted from FIG. 3, the length of the restricted portion 38 is preferably ¼ wavelength at the transmitter frequency. The broad walls at the restricted portion 38 preferably have a length from side to side of ½ wavelength. In this way the distance of tubing bobbin assembly to the end plate, or short circuit, is a ¼ wavelength transmitter frequency. Note in FIG. 3 the ¼ wavelength dimension from the center line of the tubing bobbin assembly to the end plate 43 which actually forms one of the narrow walls at the restricted portion of the waveguide member.

The reduction in width compensates for the high dielectric loading of the liquid contained in the liquid contained in the tubing. This will thus improve the bandwidth (VSWR) of the structure. The loss associated with the liquid contained in the tubing is adequate to provide a matched termination into the waveguide at the transmitter frequency. As indicated previously, the selected transmitter frequency in one embodiment is 2.45 GHz.

The length of the restricted portion taken longitudinally along the waveguide member is selected to be of sufficient length to contain the smaller waveguide 45 which operates at the higher frequency used for detection. The width of the detector waveguide 45 may be adjusted with the use of dielectric loading. The width of reduction is proportional to the square root of $\epsilon_r$ where $\epsilon_r$ is the relative dielectric constant. Thus, the waveguide structure illustrated in the drawings, with its restricted width portion provides for both heat concentration and uniformity at the heating area 39 as well as a means for accommodating the detection waveguide 45. Now, in this regard because of the high dielectric constant of blood, there is generally less depth of penetration of the microwave energy and thus the closer the energy has to preferably be to concentrate and direct the energy toward the blood path. The restricted waveguide section in accordance with the invention provides the desired concentration or focusing of energy predominantly where the tubing-bobbin assembly is inserted. In this regard refer to FIG. 6.

As indicated previously, the detection waveguide preferably operates at 4.7 GHz (i.e. twice the transmit frequency). By this manner of frequency selection, the transmit frequency is highly attenuated thus providing protection for the sensitive microwave radiometer in the circuit. Thus, by having a lower transmit frequency, this does not interfere with the detection frequency and thus the signal that is monitored is one representative of only the temperature of the fluid flowing in the IV tube.

The ability to measure temperature within the heating cavity prevents overheating of the liquid in the event of blockage or stoppage of flow. In this connection it is noted that there is an aperture 46 coupling from the heating area 39 into the waveguide 45. This aperture is sufficiently small so as not to perturb the heating characteristics at the lower heating frequency. FIG. 7 illustrates a coupling aperture at 46. Coupling may also be provided by simply leaving the entire end of the waveguide 45 open.

As indicated previously, the tubing bobbin assembly is formed by winding the plastic IV tube 12 about a cylindrical bobbin 40. Once wound, the assembly is inserted in the center of the waveguide member. The assembly may enter through the aperture in the broad wall of the heating cavity as illustrated in FIG. 3. Alternatively, all or a segment of the broad wall may be opened to accommodate the assembly. The heating of the fluid within the tubing is uniform because the absorption characteristics do not change over the narrow temperature range involved. The tubing diameter is small with respect to the wavelength of the transmit frequency, assuring adequate depth of penetration. This avoids hot spots usually found in heating fluids such as blood in conventional or even special purpose microwave ovens.

In FIGS. 3-7 there has been described primarily the details of the heating cavity, although, reference has been made to the detection waveguide 45. In this regard as noted in FIGS. 3, 5 and 6, the detection waveguide also has supported at an end thereof a waveguide-to coax transition, illustrated in FIG. 5 as including the connector 48 and associated probe 49. FIG. 5 also shows the coupling aperture 46 with the heating area 39. The waveguide 45 is dimensioned so as to transmit microwave signals at a preferred detection frequency of say 4.7 GHz. Because of the close proximity of the coupling aperture 46 to the tubing bobbin assembly, the signals that are coupled into the waveguide 45 are representative of the temperature of the fluid flowing in the IV tube 12.

As indicated previously, the main waveguide member has a restricted portion that is of a width equivalent to ½ wavelength at the detection frequency (i.e. 4.7 GHz). This greatly enhances radiometric performance, creating a point coincident with the tubing bobbin assembly of maximum E field, much like that created at the heating area by proper placement of the coax-to-waveguide transition previously discussed (refer to connector 35).

The detection waveguide 45 is illustrated in FIGS. 3 and 5 couples into the narrow wall of the heating cavity waveguide at the restricted portion 38. As indicated previously the opening or aperture 46 is small with respect to the transmit frequency and will, therefore, not perturb the transmit path. The smaller waveguide is cut off at the transmit frequency, isolating the sensitive radiometer from the microwave transmitter. As also indicated previously, the reduction in the width of the cavity brings the detection waveguide in close proximity to the liquid, such as illustrated in FIG. 6. The proper spacing of the tubing-bobbin assembly with respect to the wall opposite the detection aperture further enhances radiometric performance. In this regard refer to the wall 43 in FIG. 3 and its proximity to the tubing-bobbin assembly.

Figure 8:
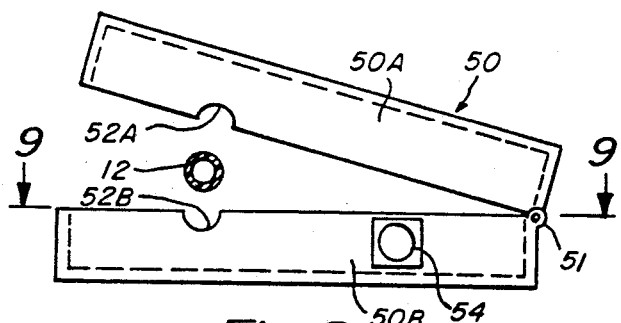
FIG. 8 illustrates one of the waveguide members for detecting either inlet or outlet temperature in a side elevation view.
Figure 9:
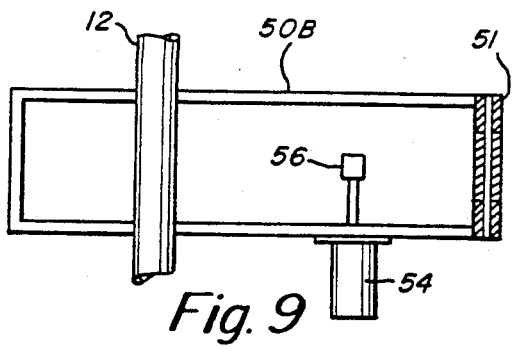
FIG. 9 is a plan view as taken along line 9—9 of FIG. 8 with the tube in place.
Figure 10:
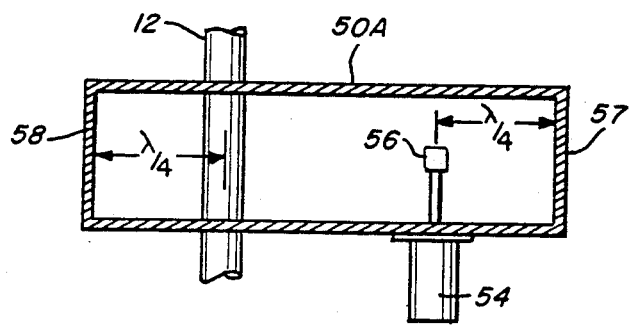
FIG. 10 is a cross-sectional view through the top portion of the waveguide of FIG. 8 also illustrating the waveguide in its closed position with the tube secured therein.

In FIGS. 3-7 reference has been made to the waveguide 45 for the detection of temperature of the liquid in the IV tube directly at the heating area of the heating cavity. It is also desired in accordance with the present invention to measure the temperature at both the fluid inlet and fluid outlet ports. In this regard, refer to the waveguide members 17A and 17B in the block diagram of FIG. 1. FIGS. 8-10 now illustrate one embodiment of a small clamp on waveguide structure that is adapted to be fitted to a mating IV tube such as the tube 12 previously referred to in the earlier drawings.

The embodiment illustrated in FIGS. 8-10 can be used either for detection of inlet temperature or outlet temperature. For this purpose there is provided a waveguide member 50 that is essentially split on its center line along its entire length without degradation of performance. In this regard, in FIG. 8 refer to the waveguide sections 50A and 50B hinged at 51. In FIG. 8 the waveguide sections 50A and 50B are shown opened so as to receive the IV tube 12. For this purpose, each of the sections is provided with a respective recess 52A and 52B. This recess is sized of a diameter to receive the IV tube 12. A securing means, not shown in the drawings, may also be employed to retain the waveguide member about the IV tube during the time that temperature measurements are to be taken.

For detecting the signals in the waveguide, there is provided a waveguide to coax transition. This includes the connector 54 and the probe 56. The probe 56 is preferably disposed ¼ wavelength from the wall 57 such as illustrated in FIG. 10. Also, the wall 58 is placed ¼ wavelength away from the liquid tubing as indicated by the ¼ wavelength illustrated in FIG. 10 measured from the wall 58. In the embodiment illustrated in FIGS. 8 10 the coaxial probe or launch is located off center, allowing the waveguide to be divided evenly along its length.

Figure 11:
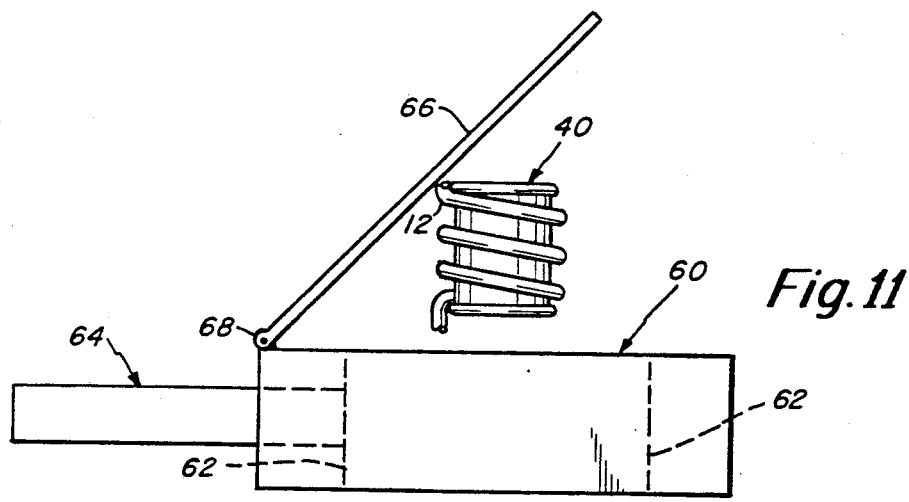
FIG. 11 is an end view of the heating cavity waveguide member showing the cavity being opened with the support means in the form of a bobbin either being inserted thereinto or removed therefrom.

FIG. 11 is an end elevation view of an alternate embodiment of the invention illustrating the main waveguide member 60 including the restricted portion 62 for receiving the detection waveguide 64. This embodiment also illustrates the IV tube 12 and the associated bobbin 40. In this particular embodiment a top wall 66 of the waveguide member 60 is hinged say at 68 so that the top wall 66 can be opened and closed. In the embodiment of FIG. 11 the tubing bobbin assembly is shown in a position in which it is either being inserted into the waveguide heating cavity or withdrawn therefrom. The bobbin 40 may be made of an inexpensive material so that it can be discarded after use with a single patient. Once the tubing-bobbin assembly has been inserted into the heating cavity, then the cover 66 is closed. The cover may have some type of a temporary locking means associated therewith for making sure that the waveguide cavity stays closed during the use of the apparatus.

Figure 12:
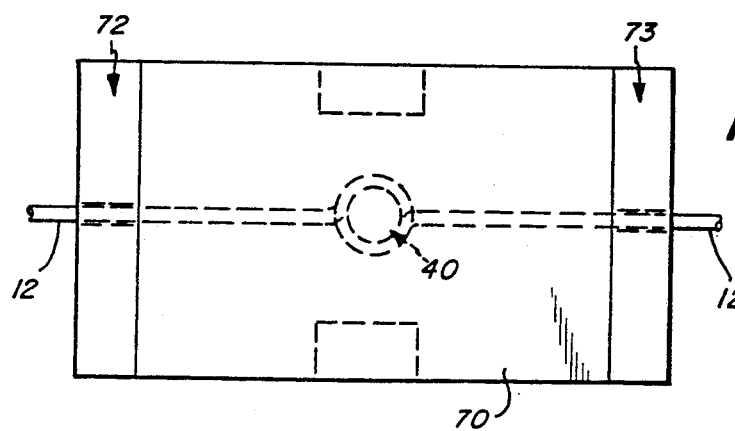
FIG. 12 is a plan view of the microwave heating cavity in an alternate embodiment including integral inlet and outlet temperature monitoring means adapted to open and close in concert with the opening and closing of the microwave heating cavity.

FIG. 12 is a plan view of an alternate embodiment of the invention in which the cover operates in unison with the inlet and outlet waveguide members. Thus, in FIG. 12 there is shown a cover 70 which forms one of the broad walls of the heating cavity. Essentially integral with this cover are the top portions of end waveguide members 72 and 73. This embodiment of the invention operates so that a single cover in essence can be opened and the tubing-bobbin assembly 40 inserted into the heating cavity while at the same time the IV tube 12 is braced in the end waveguide members 72 and 73. When the cover 70 is closed to close the heating cavity, this also, at the same time, closes the waveguide member 72 and 73 about the IV tube 12. The members 72 and 73, of course, may be similar in construction to the waveguide members described in FIGS. 8-10 and are used for monitoring inlet and outlet temperatures.

As indicated previously, and with reference to FIG. 1, a single microwave radiometer 20 is used to monitor all of the temperatures that have been referred to. These different temperature signals, via feedback control 18 in FIG. 1, then control the microwave transmitter 14 to determine the output thereof for in turn controlling the heat applied at the microwave heating cavity. In this regard, refer to FIGS. 13 and 14 for further details of the feedback control.

In FIG. 1 the switch 22 is shown coupling to the radiometer 20. The switch 22 may be considered as the equivalent to a single pole three throw mechanical switch coupling in seguence the cavity, inlet and outlet temperature signals to the radiometer 20. The radiometer 20 is preferably a DICKE radiometer circuit as will be described in further detail in connection with FIG. 15.

Figure 13:
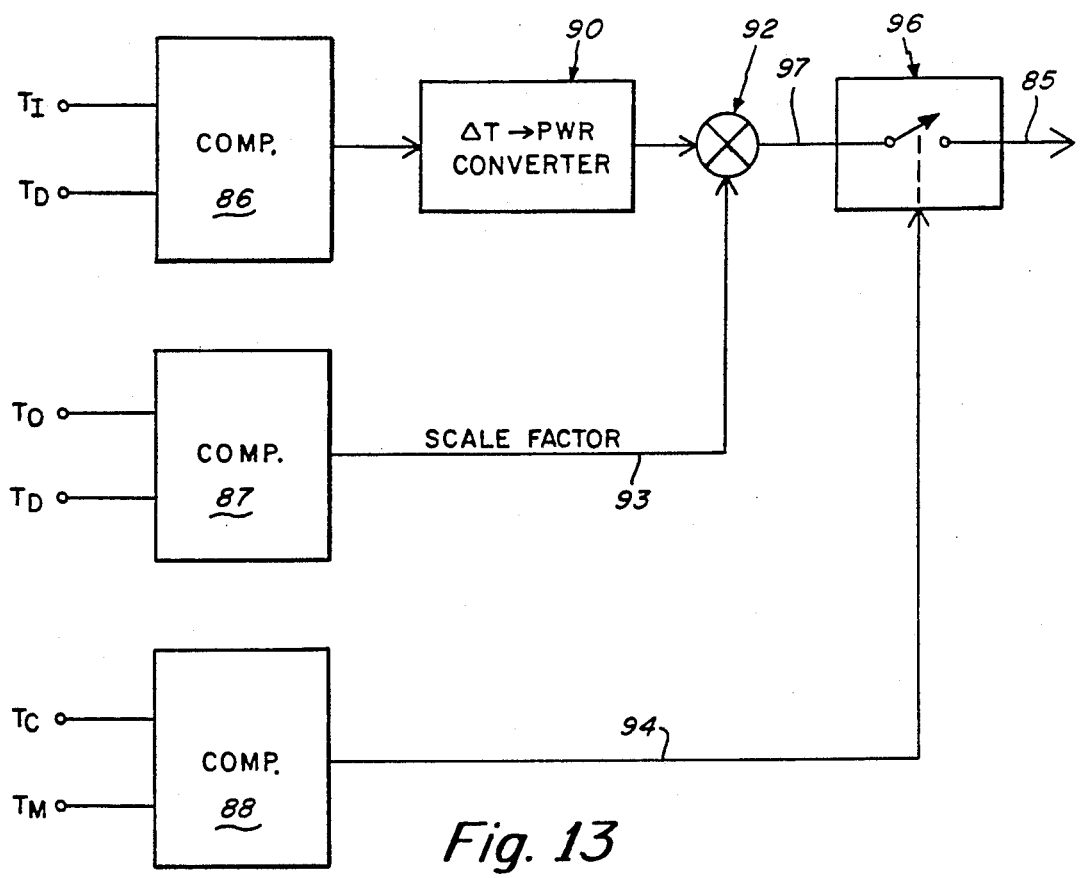
FIG. 13 is a circuit block diagram of a portion of the control unit, illustrated in FIG. 1 as a feedback control.
Figure 14:
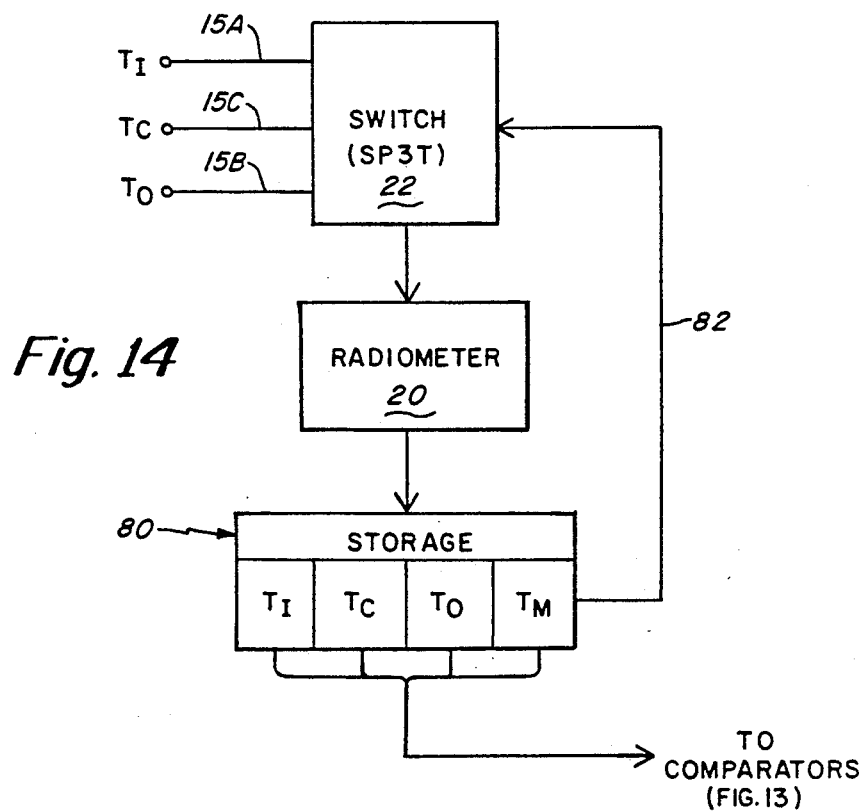
FIG. 14 is a further block diagram of the control of the present invention including a microwave radiometer circuit.

FIG. 14 also shows a storage device or memory device 80 that is adapted to store electrical signals representative of the different temperatures sensed. This is illustrated in FIG. 14 by the temperatures $T_I$ for input temperature, $T_C$ for heating cavity temperature and TO for outlet temperature. Also illustrated is the temperature $T_M$ which is a preset level indicating a maximum temperature beyond which the cavity is to not heat the liquid. This may be set so that the cavity temperature does not exceed say 46° C. Also, is the signal, not illustrated in FIG. 14 which is the signal $T_D$ which indicates the desired temperature. This is the parameter that is set, per FIG. 2, by the dial 26 on the power and control unit 24. All of the circuitry shown on FIGS. 13 and 14 may be considered as contained in the power and control unit 24. It is furthermore noted that there is a feedback line 82 coupling from the storage unit 80 back to the switch 22. This simply provides coordination between which of the radiometer signals are stored as it relates to the particular switch setting at that time. Thus, for one instance in time the switch 22 couples signals from line 15A to the radiometer. This causes a storage in a memory an electrical signal representative of input temperature. At a later instance in time the switch 22 may be coupling signals to the radiometer 20 from one of the other inputs in which case the storage is in a different memory location to store a signal representative of the other temperature parameter. FIG. 14 shows these temperature signals coupling to the comparators of FIG. 13.

Reference is now made to the block diagram of FIG. 13 for an illustration of the control circuitry that is responsive to the different temperature signals for providing an output control signal at line 85 that may be coupled to the microwave transmitter for controlling the output of the microwave transmitter signal. In FIG. 13 there are shown three comparators 86, 87 and 88. The output of comparator 86 couples to a converter 90. The output of the converter couples to a multiplier 92 which also receives a signal from the output of comparator 87 by way of line 93. The output of the multiplier 92 couples to an analog switch 96 that receives a control input by way of line 94 from the comparator 88.

In FIG. 13 both of the comparators 86 and 87 receive signals indicating the desired temperature level. These are the signals $T_D$. The comparator 86 also receives the input temperature signal $T_I$. The comparator 87 also receives the outlet signal $T_O$. The comparator 88 receives the temperature indicating cavity temperature which is temperature $T_C$ and also receives the signal $T_M$ which indicates maximum desired cavity temperature that is not to be exceeded.

In FIG. 13, as long as the input temperature is less than th desired temperature then the output of the comparator 86 operates a temperature-to-power converter 90 for providing a predetermined level signal to the multiplier 92. This signal is multiplied by a scale factor coupled on line 93 from the comparator 87. The comparator 87 compares output temperature to the desired temperature. If the output temperature is less than the desired temperature by a substantial amount then there is a corresponding substantial scale factor for multiplication purposes so that the output signal on line 97 from the multiplier is a function of the particular scale factor on line 93. If the output temperature is close to the desired temperature then the scale factor is less and thus the multiplication is less meaning that the signal on line 97 is thus scaled down. The operation is such as to control the amplitude of a signal coupled by way of switch 96 to output control line 85 depending upon certain input temperature parameters. Thus, when the output temperature approaches the desired temperature the scale factor reduces which in turn indicates that the power being coupled into the heating cavity is gradually decreased as the desired temperature is approached. Now, if excessive heating occurs at the cavity, this is detected by the comparator 88 and a signal is sent on line 94 to open the analog switch 96. When the cavity temperature is less than the maximum temperature then the signal on line 94 keeps the switch 96 in a closed position enabling the multiplied signal on line 97 to be coupled directly to the control line 85 for controlling the output of the microwave transmitter.

Reference has been made hereinbefore to the radiometer 20 of FIG. 1. Now, reference is made to FIG. 15 which shows a schematic circuit diagram of a microwave radiometer that may be employed in the system of this invention for taking temperature measurements. Preferably, a single radiometer is employed and readings are taken in succession from each of the waveguide members as will be described hereinafter.

Figure 15:
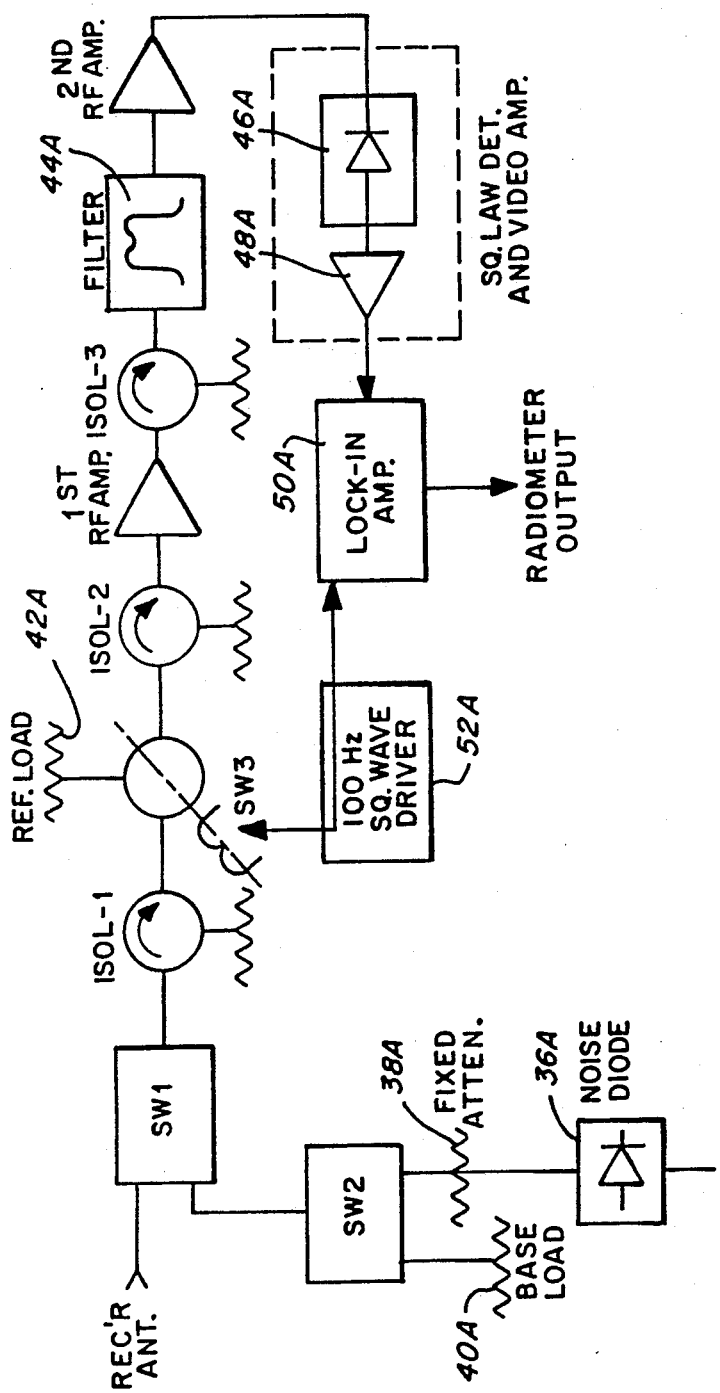
FIG. 15 illustrates one embodiment of a radiometer circuit.

With regard to FIG. 15, there is illustrated an input to the switch SW1 from the switch 22. The microwave radiometer that is depicted may be of the DICKE switch type. The radiometer design substantially reduces the effects of short term gain fluctuations in the radiometer. The receiver input is switched by means of a switch SW1 at a constant rate between the antenna and a constant temperature reference load. The switched, or modulated RF signal is therefore inserted at a point prior to RF amplification and as close to the antenna as possible; in turn, it is then amplified and coherently detected. The final output is proportional to the temperature difference between the antenna and the reference load.

In FIG. 15 a second switch SW2, referred to as a calibration switch, may also be employed. With this switch, the reference load as defined by the noise diode 36A and fixed attenuator 38A, is compared with a base load 40A rather than with the signal from the antenna. If the base load is equal in temperature with the reference load, the DC output of the radiometer is thus nulled to zero.

The radiometer described herein employs at least one low noise RF amplifier in conjunction with a simple single ended square law detector rather than the more complex superheterodyne which employs a local oscillator and IF amplifier. The square law detector of this arrangement minimizes the potential drift and noise associated with the superheterodyne approach. The conformance that comprises the radiometer are discussed in detail hereinafter. With regard to the microwave radiometer schematic of FIG. 15, at its input there is shown the connection which is preferably by way of a coax cable from the waveguide member to one input of switch SW1. This may be termed a calibration switch which is a solenoid-operated, mechanical single pole/double-throw switch used to disconnect the antenna and in its place connect the base load 40A by way of a second switch SW2. The switch SW1 has an isolation or switching radio, of greater than 60 dB with a corresponding insertion loss of less than 0.1 dB. The switch SW2 is used in the calibration circuit to disconnect the base load and to insert in its place the calibrated noise source as represented by the fixed attenuator 38A and the noise diode 36A referred to hereinafter.

As indicated in FIG. 15, there are three ferrite isolators used in the receiver path. These are identified as isolators ISOL-1, ISOL-2 and ISOL 3. The first isolator, is located between the calibration switch SW1 and the DICKE switch SW3. This isolator is used to terminate the output of the reference load when the DICKE switch is in the low loss state. In this state, the reference or base load is circulated in the direction of the antenna which, in this case, functions as a ferrite isolator. The isolator ISOL 1 employs a coaxial to-waveguide transition. The insertion loss of this isolator and the transition is less than 0.2 dB, with a corresponding isolation of greater than 2.3 dB.

The second isolator ISOL 2 in FIG. 15, is disposed between the switch SW3 and the first stage RF amplifier to maintain a constant load match to this amplifier. Any reflections from the RF amplifier would therefore be terminated in the isolator. Again, this isolator, which is a waveguide isolator with a coax-to-waveguide transition, has an insertion loss of less than 0.2 dB with an isolation of greater than 23 dB.

There is also provided in FIG. 15 a third isolator ISOL-3 which is located between the output of the first RF amplifier and the bandpass filter 44A. The purpose of this particular isolator is to present a constant load match to the output stage of the first RF amplifier, and also to present a matched input to the bandpass filter 44A.

A switchable ferrite circulator, designated switch SW3 in FIG. 15, forms the load comparison, or DICKE switch, function. A ferrite device is preferred over a semiconductor approach primarily in view of the lower insertion loss, typically less than 0.3 dB, and elimination of noise generated by the semiconductor junction over and above the measured insertion loss.

Briefly, the device SW3 is a switchable ferrite junction circulator utilizing the remnant, or latching, characteristics of the ferrite material. The principle of latching action is as follows: Using the intrinsic properties of a hysteresis loop of a ferrite toroid, a transverse magnetic field is used across a portion of the ferrite exposed to an RF signal. The biasing field is actually the residual inductance of the ferrite toroid; therefore, the device needs no holding power and can be reversed in polarity using merely enough energy to overcome the natural coercive force of the toroid.

For the system of this invention, the latching circulator has been constructed in waveguide having a single ferrite element contained within the microwave circuit. The insertion loss is less than 0.3 dB, having isolation in excess of 20 dB.

The first stage RF amplifier may be a four stage FET device constructed in microstrip with integrated biasing circuitry. The noise figure of the first amplifier (M/A Canada amplifier Model No. MC 2019) is 2.0 dB with a gain of 35 dB. The second RF amplifier Amplica Model No. 3441CS) has a noise figure of 2.6 dB, with an associated gain of 33 dB. In both instances, the noise figure includes the input ferrite isolator as depicted in FIG. 15. With the input and output VSWR at less than 1.5:1, the gain compression at signal levels of between $-55$ dbm to $-10$ dbm is less than 0.1 dB.

In FIG. 15 the filter 44A is a bandpass filter and the bandwidth of the microwave radiometer is basically determined by the bandpass characteristics of this filter. The filter is disposed after the first stage of RF amplification to minimize the impact of the insertion loss of the filter on the overall system performance. The filter characteristics are chosen to minimize possible interference due to nearby microwave communications or radar bands. The filter is preferably an 8-section bandpass filter constructed in stripline. The pass band loss is less than 3 dB and the bandwidth is approximately 500 MHz.

As indicated in FIG. 15, there are basically two loads provided, a base load 40 and a reference load 42A. The load design is coaxial, employing a stainless steel RF connector to provide thermal isolation between the load and the remainder of the system. The coaxial termination is contained within an insulated housing and utilizes an integrated heater and proportional control to maintain constant temperature. The absolute temperature of both the base and the reference loads is monitored and displayed on a digital temperature indicator (not shown).

The calibration circuit comprises a precision, solid state, noise source having an excess noise ratio, ENR of 33 dB. This allows noise to be injected into the receiver front end via the high isolation mechanical calibration switch. The output level of the noise source is reduced through the use of a precision calibrated pad (43.3 dB). This calibration circuit is shown in FIG. 15 as including a fixed attenuator 38A and the noise diode 36A.

The lock-in amplifier 50A shown in FIG. 15 enables the accurate measurement of signals contaminated by broad band noise, power line pickup, frequency drift or other sources of interference. It accomplishes this by means of an extremely narrow band detector which has the center of its pass band locked to the frequency of the signal to be measured. Because of the frequency lock and narrow bandwidth, large improvements in signal to-noise ratio are achieved. This allows the signal of interest to be accurately measured, even in situations where it is completely masked by noise. In addition, the lock-in amplifier 50A provides the synchronous function associated with the DICKE switch; i.e., the unit supplies the 100 Hz reference clock frequency to drive the ferrite switch driver.

The system is provided, of course, with a power supply comprising two 12-volt 50 amp maintenance free, lead acid batteries in series, fused at 10 amps per battery. The outputs from the battery assembly include 12 and 24 volts. These voltages are appropriately applied to the receiver and lock in amplifier. There may also be provided a voltage converter and regulator. Status indicators may be employed for indicating operating voltages. The main operating switch may have three positions including an on position, an off position and a "charged" position. In the charged mode, a meter is used to monitor the charge current to the batteries which is limited to approximately 6 amps. With a 3–6 amp-hour discharge rate (a normal 12 hour operating mode), the recharge cycle is approximately 10–12 hours (overnight).

Reference is now made to FIGS. 16A–16D regarding an alternate embodiment of the invention employing a unique packaging for the apparatus that enables the apparatus to be easily opened for receipt of the tubing-bobbin assembly. This alternate embodiment essentially splits the heating cavity along its length to minimize possible leakage from the waveguide. The device includes a provision for cavity, inlet and outlet temperature detection. In this connection, the three detector waveguides are contained in a die cast housing including a hinge arrangement.

One of the advantages of the embodiment described in FIGS. 16A–16D is that the two halves of the housing are substantially identical resulting in a simple single cavity die. The dimensions of the detector waveguide are based upon the dielectric constant of the material used within the waveguide.

With respect to the tubing-bobbin assembly, this can be injection molded and may also contain a portion of the detector waveguide dielectric as to be described hereinafter. The bobbin itself is fabricated inexpensively as it is intended that this along with the integral detector waveguide dielectric be disposable.

Figure 16A:
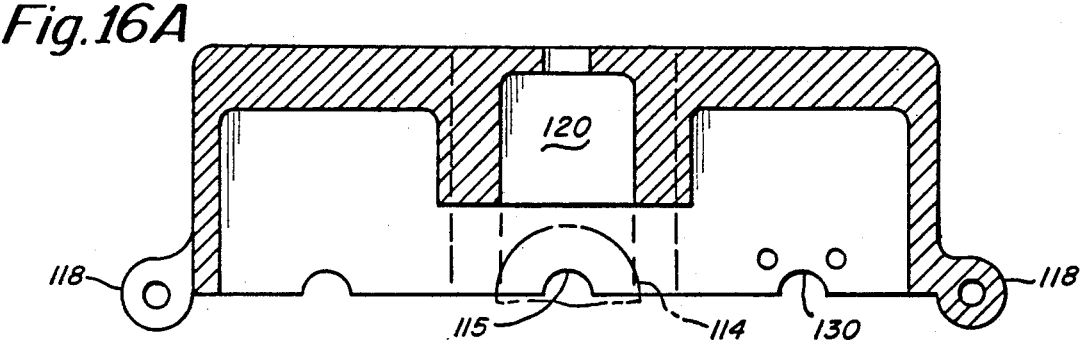
FIGS. 16A-16D are separate views illustrating a further embodiment of the present invention providing an integral unit for cavity, inlet and outlet temperature monitoring.
Figure 16B:
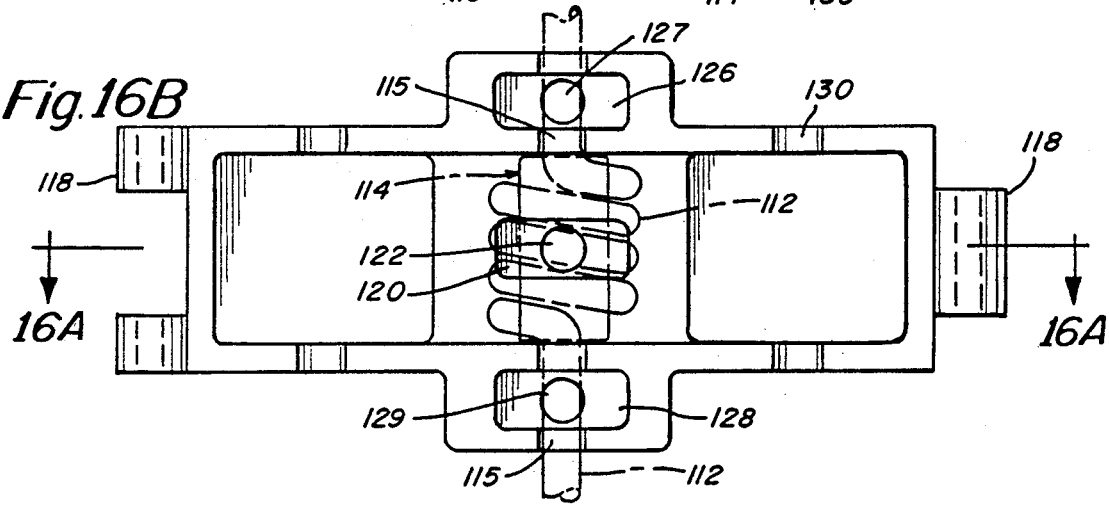
Figure 16C:
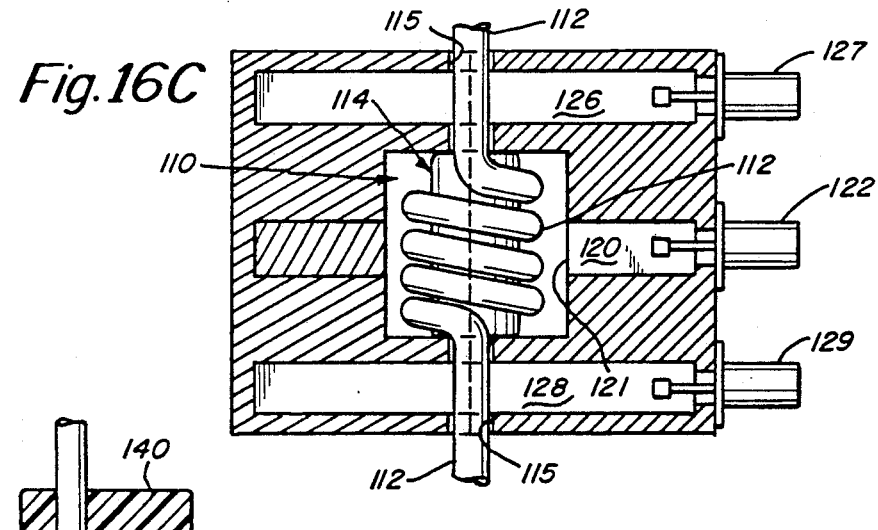
Figure 16D:
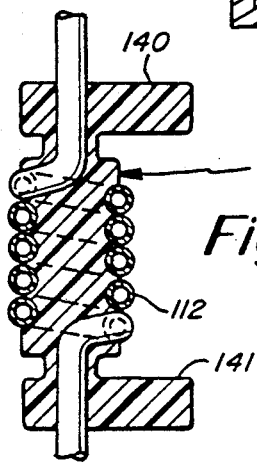

Reference is now made in particular to FIGS. 16A–16D. FIG. 16B is a front view of one half of the housing that comprises the waveguide member. FIG. 16A is a cross sectional view taken along line 16A—16A of FIG. 16B. FIG. 16C is a partial cross-sectional side view illustrating the multiple detector waveguides for inlet, outlet and cavity temperature. FIG. 16D shows the tubing-bobbin assembly.

Thus, in FIGS. 16A–16D there is provided a heating cavity 110. FIG. 16B and 16C illustrate the intravenous tube 112 disposed about the bobbin 114 and extending through passages provided in the microwave heating cavity 110. In this regard note in FIG. 16B the passages at 115 sized to receive the IV tube 112. FIGS. 16A and 16B also illustrate the hinging at at 118 which enables two halves to be hinged so that the waveguide cavity can be opened for insertion of the tubing-bobbin assembly.

With respect to FIG. 16C it is noted that the tubing bobbin assembly is in position in the heating cavity. FIG. 16C also shows the detector waveguide 120. Also note FIG. 16B. This has a coupling aperture at 121. Also illustrated in FIG. 16C is the output port at 122 from which a signal is derived indicative of cavity temperature. This may be a waveguide-to-coax transmission.

FIG. 16C also shows the integral waveguide members 126 and 128. The waveguide 126 is for measuring inlet temperature. The waveguide 128 is for measuring outlet temperature. Each of these have associated therewith output ports 127 and 129 respectively. Each of these output ports may be in the form of a connector and probe as referred to hereinbefore. These may be in the form of a waveguide-to-coax transition.

In the embodiment of FIGS. 16A–16D there is also provided an input to the heating cavity at one end thereof. A probe arrangement as described previously may be used. The two halves of the waveguide member are fabricated with holes such as at 130. However, it is noted that some of these holes may be blocked off while at one of the holes and appropriate coupling is provided such as a coax-to-waveguide transition for coupling power into the heating cavity. In this regard refer to FIGS. 3 and 4 previously described.

Reference is now made to FIG. 16D. This illustrates the bobbin 114 that has ends 140 and 141. The IV tube 112 goes through a passage in each of these ends and winds about the bobbin. In this way the IV tube is secured in place. The IV tube is then placed in the accommodating passages 115 so that the IV tube extends through the inlet and outlet waveguide members such as is illustrated in FIG. 16C. It is noted that the ends 140 and 141 of the bobbin 114 are elongated so as to extend into the waveguide members 126 and 128. This provides for automatic dielectric filling of these waveguide members. The bobbin may also be provided with an extension in the middle thereof for filling the waveguide member 120.

Having now described a number of embodiments and aspects of the present invention it should now be apparent to those skilled in the art that numerous other embodiments and modifications thereof are contemplated as falling within the scope of the present invention as defined by the appended claims.

What is claimed is:

1. Microwave apparatus for the warming of a liquid flowing in a liquid conduit, said apparatus comprising: a microwave heating cavity, means for applying microwave energy at a selected power level to said microwave heating cavity, means for supporting a length of said liquid conduit in said microwave heating cavity extending between input and output sides thereof, microwave energy being applied to the conduit and to the fluid flowing therein, non-invasive temperature monitoring means for measuring the temperature of a liquid flowing in the liquid conduit at said cavity, said means for supporting a length of said liquid conduit comprising a support member that supports a predetermined length of said liquid conduit within the cavity wherein said predetermined length is greater than the distance between the input and output sides of said cavity so as to enhance heating action, and control means responsive to said measured temperature for controlling the power of said means for applying microwave energy.

2. A device for detecting the temperature of a fluid flowing in a conduit, which conduit is transparent to microwave energy comprising:
 a single waveguide structure having first and second walls;
 means for defining a first opening formed in said first wall of the waveguide and means defining a second opening formed in said second wall of the waveguide, said second wall being disposed relative to the first wall in a manner to permit the conduit to pass therebetween;
 a coaxial probe mounted in said waveguide and spaced from the conduit passing through the waveguide;
 a radiometer; and
 means for connecting the probe output to the radiometer;
 radiation detected by the probe being proportional to the temperature of fluid in the portion of the conduit passing through the waveguide.

3. A device as set forth in claim 2 wherein save waveguide structure includes means for opening the waveguide to permit the conduit to be fitted therein.

4. A device as set forth in claim 2 including means for operating the probe and radiometer at a predetermined microwave frequency.

5. A device as set forth in claim 4 wherein said conduit is spaced substantially one quarter wavelength at said microwave frequency from a nearest wall of the waveguide, and wherein said probe is spaced substantially one quarter wavelength from a nearest wall thereto of the waveguide.

6. Microwave apparatus for warming of a liquid flowing in a liquid conduit, said apparatus comprising a microwave energy sauce, having an output signal: a microwave heating cavity, means for applying microwave energy at a selected power level from said microwave source to said microwave heating cavity, means for supporting a selected length of said liquid conduit in said microwave heating cavity, microwave energy being applied to the conduit and to the fluid flowing therein, non-invasive microwave temperature monitoring means for directly measuring the temperature of liquid flowing in said liquid conduit at said cavity and at at least one of an inlet to the cavity and an outlet therefrom, means for selecting a desired operating temperature, and control means responsive to the desired operating temperature and to all measured temperatures for controlling the power of the microwave energy.

7. Microwave apparatus as set forth in claim 6 wherein said microwave heating cavity comprises a first waveguide member and the means for applying said microwave energy to said microwave heating cavity comprises a probe disposed at one end of the waveguide member.

8. Microwave apparatus as set forth in claim 7 wherein said first waveguide member has a restricted portion disposed along a length thereof defining a concentrated and uniform heating area at which is disposed said means for supporting a length of said liquid conduit.

9. Microwave apparatus as set forth in claim 8 wherein said temperature monitoring means comprises a second waveguide member coupled into said heating area.

10. Microwave apparatus as set forth in claim 9 wherein said probe in the first waveguide member comprises part of a coax-to-waveguide transition.

11. Microwave apparatus as set forth in claim 10 wherein said restricted portion is disposed midway along said first waveguide member.

12. Microwave apparatus as set forth in claim 11 wherein said temperatures monitoring means includes a radiometer circuit means coupled from said second waveguide member for sensing temperature at said hearing area.

13. Microwave apparatus as set forth in claim 12 wherein said radiometer circuit means connects to said microwave source to control the output signal thereof as a function of at least the temperature sensed at said heating area.

14. Microwave apparatus as set forth in claim 13 wherein said temperatures monitoring means includes a waveguide-to-coax transition means at an end of the second waveguide member for coupling signals detected from said heating area.

15. Microwave apparatus as set forth in claim 14 wherein the means for applying microwave energy includes means for operating at a predetermined heating frequency and said temperature monitoring means includes means for sensing at a different radiometer detection frequency.

16. Microwave apparatus as set forth in claim 15 wherein the detection frequency is greater than the heating frequency.

17. Microwave apparatus as set forth in claim 8 wherein said means for supporting a length of said liquid conduit comprises a bobbin means for receiving the liquid conduit wound about the bobbin means.

18. Microwave apparatus as set forth in claim 5 wherein said bobbin means and the conduit wound thereabout comprise a bobbin assembly, and including means for removably mounting said bobbin assembly.

19. Microwave apparatus as set forth in claim 17 wherein said first waveguide member includes means for opening said first waveguide member so as to receive said bobbin means and so as to enable removal of said bobbin means.

20. Microwave apparatus as set forth in claim 17 wherein said temperature monitoring means further includes a third waveguide member at the inlet side of the heating cavity for detecting a liquid conduit inlet temperature;
and wherein said control means is also responsive to the detected inlet temperature.

21. Microwave apparatus as set forth in claim 20 wherein said temperature monitoring means further includes a fourth waveguide member at the outlet side of the heating cavity for detecting liquid conduit outlet temperature;
and wherein said control means is also responsive to the detected outlet temperature.

22. Microwave apparatus as set forth in claim 21 wherein both said third and fourth waveguide members couple to said radiometer circuit means.

23. Microwave apparatus as set forth in claim 6 wherein said temperature monitoring means includes waveguide means for monitoring liquid temperature at an inlet to said microwave heating cavity;
and wherein said control means is also responsive to the detected inlet temperature.

24. Microwave apparatus as set forth in claim 23 wherein said temperature monitoring means includes waveguide means for monitoring liquid temperature at an outlet from said microwave heating cavity;
and wherein said control means is also responsive to the detected outlet temperature.

25. Microwave apparatus as set forth in claim 24 wherein said control means includes a means for setting a signal indicative of a desired temperature of liquid warming.

26. Microwave apparatus as set forth in claim 25 wherein said control means includes first comparator means responsive to inlet temperature ($T_I$) and desired temperature ($T_D$) for providing an intermediate power level signal.

27. Microwave apparatus as set forth in claim 26 wherein said control means includes second comparator means responsive to outlet temperature ($T_O$) and desired temperature ($T_D$) for providing a scaling signal, a multiplier means for receiving both said intermediate signal and said scaling signal, third comparator means responsive to cavity temperature ($T_C$) and maximum temperature ($T_M$) for providing an inhibit signal, and switch means controlled by said inhibit signal for selectively passing the output of said multiplier means.

28. Microwave apparatus as set forth in claim 6 wherein said microwave heating cavity comprises two separate housing members and means for allowing said housing members to open.

29. Microwave apparatus as set forth in claim 28 wherein said means for supporting comprises a bobbin with said housing members hinged upon a hinge line that extends in the same direction as the axis of said bobbin.

30. Microwave apparatus as set forth in claim 29 wherein said bobbin includes a dielectric in combination with waveguide means for monitoring liquid temperature at an inlet to the microwave heating cavity, said waveguide means also for monitoring liquid temperature at an outlet of the microwave heating cavity, said dielectric including means for extending into and filling at least part of said waveguide means for monitoring inlet and outlet temperature.

31. A system as set forth in claim 6 wherein said control means includes first comparator means responsive to inlet temperature ($T_I$) and desired temperature ($T_D$) for providing an intermediate power level signal.

32. A system as set forth in claim 31 wherein said control means includes second comparator means responsive to outlet temperature ($T_O$) and desired temperature ($T_D$) for providing a scaling signal.

33. A system as set forth in claim 32 wherein said control means includes a multiplier means for receiving both said intermediate signal and said scaling signal and developing an output.

34. A system as set forth in claim 33 wherein said control means includes third comparator means responsive to cavity temperature ($T_C$) and maximum temperature ($T_M$) for providing an inhibit signal.

35. A system as set forth in claim 34 including switch means controlled by said inhibit signal and for selectively passing the output of said multiplier means.

36. A method of warming a liquid flowing in a liquid conduit by means of a microwave heating cavity having microwave energy coupled thereto from a microwave transmitter, said method comprising the steps of, providing at least a part of the heating cavity that can be opened and closed, providing a support assembly including a length of said liquid conduit, disposing said support assembly in said cavity, closing said cavity, applying controlled microwave energy to said cavity to cause liquid warming as the liquid flows through the cavity, monitoring the liquid temperature at the cavity and at at least one of the input and output thereto, selecting a desired liquid temperature and controlling the energy coupled to said cavity in response to the selected liquid temperature and the monitored temperature to maintain a desired liquid temperature.

37. A method as set forth in claim 36 wherein said temperature monitoring step includes the step of monitoring temperatures of liquid flowing in the cavity, of liquid at the inlet to the cavity and of liquid at the outlet thereto utilizing, the monitored temperatures to control microwave energy coupled to said cavity.

38. A method as set forth in claim 37 including winding the length of conduit on the support assembly.

39. A method as set forth in claim 36 including the steps of opening the cavity when a warming operation is complete, removing the support means and length of liquid conduit therefrom, replacing the removed support means and conduit with an unused support means and conduit, and closing the cavity.

40. A method as set forth in claim 39 including the step of disposing of the removed support means and conduit.

* * * * *

UNITED STATES PATENT AND TRADEMARK OFFICE
CERTIFICATE OF CORRECTION

PATENT NO. : 5,073,167
DATED : December 17, 1991
INVENTOR(S) : Carr et al.

It is certified that error appears in the above-indentified patent and that said Letters Patent is hereby corrected as shown below:

On the title page, item [75] Inventors: the following inventor should be deleted:

--Steven D. Schwailzberg, Chestnut Hill,--.

Signed and Sealed this

Twenty-ninth Day of November, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,073,167
DATED : December 17, 1991
INVENTOR(S) : Carr et al.

It is certified that error appears in the above-indentified patent and that said Letters Patent is hereby corrected as shown below:

On the title page, item [75] Inventors: the following inventor should be deleted:

--Steven D. Schwaitsberg, Chestnut Hill,--.

This certificate supersedes Certificate of Correction issued November 29, 1994.

Signed and Sealed this

First Day of August, 1995

Attest:

BRUCE LEHMAN

Attesting Officer

Commissioner of Patents and Trademarks